United States Patent
Rahn et al.

(10) Patent No.: US 6,806,864 B2
(45) Date of Patent: Oct. 19, 2004

(54) OPERATING DEVICE FOR INFLUENCING DISPLAYED INFORMATION

(75) Inventors: Norbert Rahn, Forchheim (DE); Siegfried Wach, Hoechstadt (DE)

(73) Assignee: Siemens Aktiengesellschaft, München (DE)

( * ) Notice: Subject to any disclaimer, the term of this patent is extended or adjusted under 35 U.S.C. 154(b) by 247 days.

(21) Appl. No.: 09/726,408

(22) Filed: Dec. 1, 2000

(65) Prior Publication Data

US 2001/0002830 A1 Jun. 7, 2001

(30) Foreign Application Priority Data

Dec. 3, 1999 (DE) .......................... 199 58 443

(51) Int. Cl.$^7$ .............................................. G09G 5/08
(52) U.S. Cl. ........................ 345/158; 345/159; 345/172; 345/419; 345/426; 345/427; 128/870; 600/409; 600/415
(58) Field of Search ............................. 345/158, 159, 345/172, 6, 419, 426, 427; 128/870; 600/409, 415

(56) References Cited

U.S. PATENT DOCUMENTS

| | | | | |
|---|---|---|---|---|
| 5,347,306 A | * | 9/1994 | Nitta .......................... | 348/14.1 |
| 5,436,542 A | * | 7/1995 | Petelin et al. ................ | 318/567 |
| 5,742,331 A | * | 4/1998 | Uomori et al. ................ | 348/51 |
| 5,855,074 A | * | 1/1999 | Abitbol et al. ................ | 33/507 |
| 6,067,075 A | * | 5/2000 | Pelanek ...................... | 345/158 |
| 6,173,194 B1 | * | 1/2001 | Vanttila ...................... | 455/566 |
| 6,219,032 B1 | * | 4/2001 | Rosenberg et al. .......... | 345/157 |
| 6,243,503 B1 | * | 6/2001 | Teufel et al. ................ | 382/312 |
| 6,292,172 B1 | * | 9/2001 | Makhlouf .................... | 345/157 |
| 6,341,179 B1 | * | 1/2002 | Stoyle et al. ................ | 382/254 |
| 6,567,032 B1 | * | 5/2003 | Mullaly et al. ............. | 341/176 |
| 6,567,984 B1 | * | 5/2003 | Allport ....................... | 725/110 |

* cited by examiner

*Primary Examiner*—Xiao Wu
*Assistant Examiner*—Abbas Abdulselam
(74) *Attorney, Agent, or Firm*—Schiff Hardin LLP

(57) ABSTRACT

An operating device for influencing medical image information items displayed at a display surface with a movable operating element has a motion acquisition system for quantitatively determining adjustment motions of the operating element, with the representation of the image information items displayed at the display surface being influenced solely by motions of the operating element.

17 Claims, 2 Drawing Sheets

OPERATING DEVICE FOR INFLUENCING DISPLAYED INFORMATION

BACKGROUND OF THE INVENTION

1. Field of the Invention

The present invention relates to an operating device for influencing image information displayed on a display surface with a movable operating element and with means for the quantitative determination of adjustment (displacement) motions of the operating element.

2. Description of the Prior Art

In image processing, particularly medical image processing, image information items, such as tomograms or 3D visualizations of three-dimensional anatomic objects, which are acquired with the aid of diagnostic devices and visualization computers, are displayed at display surfaces for diagnosis, therapy or operation planning. In order to influence the manner by which the image information items are displayed, one or more input means, such as a keyboard, a joystick, a trackball or mouse, are normally connected to the visualization computer. By manipulating the mouse and/or other equivalent input means, a marker that is faded into displayed image information can be moved relative to the image information (known as "zoom"), a selection of a number of displayed image information items, or a scrolling through different views of image information items can be undertaken.

For example, PCT Application WO 97/15840 describes a medical imaging system with an input device, which is fashioned such that the sequence parameters can be modified by set-up means during a sequence. The set-up means can include a joystick, a mouse or a track ball, for example.

German OS 198 19 218 describes an operating element that is preferably fashioned as a handheld operating element and that essentially exhibits the functionality of a joystick.

U.S. Pat. No. 5,506,605 discloses a three-dimensional mouse, which can be freely moved in space.

Furthermore, European Application 0 429 391 describes an input device for a computer, which also exhibits the functionality of a three-dimensional mouse.

U.S. Pat. No. 5,303,148 describes a voice-operated medical and imaging system. The input ensues, for example, by means of a microphone, whereby the system commands activate procedures that are preprogrammed and stored in a computer.

German OS 195 01 581 discloses a foot-operable input device for medical-technical system workstations, particularly for surgery.

German OS 197 40 382 describes a movable electronic component, which is provided with keys, which can be operated from outside and by means of which the function of the component can be controlled. This component can be particularly fashioned as a waterproof computer mouse.

It has proven disadvantageous that the known input means normally are two-dimensionally adjustable input means that are bound to a specific operating location, so that it is often difficult to transfer image information items, particularly three-dimensionally visualized image information items, from one view into another view in a simple way with the aid of such input means.

A three-dimensionally displayed object is rotated by means of a mouse, for example, such that the marker, which is shown at the display surface and which is coupled to the mouse, is positioned onto a point of the object, which is shown at the display surface and which is to be rotated, by corresponding motions of the mouse. Given a simultaneous actuation of a key of the mouse, the mouse is perpendicularly moved to the rotational axis around which the object is to be rotated, effecting the rotation of the object. This type of utilization of the mouse for rotating a three-dimensionally visualized object is referred to as a "virtual trackball". It is not easy for the user to get accustomed to the operation of the virtual trackball. Moreover, the user can easily loose his or her orientation regarding the current orientation of the object after a few rotation actions with respect to complex three-dimensionally displayed objects.

SUMMARY OF THE INVENTION

An object of the present invention is to provide an operating device of the aforementioned type wherein the handling of the operating device proceeds intuitively for the user.

This object is inventively achieved in an operating device for influencing medical image information items, which are displayed at a display surface, with a movable operating element and with means for quantitatively determining adjustment motions of the operating element, wherein the display of the medical image information items displayed at the display surface can be influenced solely by motions of the operating element alone. The inventive operating device therefore is fashioned such that the means for determining adjustment motions, which preferably include a calculating unit by means of which adjustment motions are quantitatively determined, acquires motions of the operating element and converts these into control signals for influencing the display of the image information items, so that the display of medical information items displayed at the display surface can be modified without further activities of a user handling the operating element, i.e., without simultaneously operating an operating element, solely by motions of the operating element in a specific direction and around a specific adjustment scope. For example, the display can be scrolled between different views of an object displayed at the display surface simply by moving the operating element or a corresponding rotation of an object displayed at the display surface can be effected by rotating the operating element. Since a motion of the operating element thus effects an influence on the display of a medical image information corresponding to the motion, an intuitive and therefore facilitated handling of the operating device results for the user.

In a particularly preferred embodiment of the invention the operating element can be freely moved in six degrees of freedom. As a result of the free movability of the operating element, there are no restrictions regarding the handling of the operating element. The free movability of the operating element has proven to be particularly advantageous for influencing the display of three-dimensionally visualized objects, since each motion of the operating element is followed by a corresponding motion of the three-dimensionally visualized object. Therefore, the user can understand every motion of the object, since an immediate relation between the motion of the operating element and the motion of the object on the display surface is always present.

In a version of the invention the operating element of the operating device has a number of operating actuators which respectively allow the operation of the operating device in different operating modes.

In a version of the invention, the operating element thereby has at least four operating actuators. The actuation of a first operating actuator places the operating device in a selection mode, in which a marker, which is mixed into a displayed image information, is moved relative to the image information, and a selection can be made by actuating the operating actuator again. The actuation of a second operating actuator places the operating device in a second operating mode, in which the size of an item of image information, which is displayed at a display surface, can be influenced solely by moving the operating element. A third operating mode of the operating device can be activated by a third operating actuator, whereby corresponding motions of the medical image information displayed at the display surface are effected by motions of the operating element. The actuation of a fourth operating actuator places the operating device in a fourth operating mode, in which scrolling between different views of image information items, which can be displayed at the display surface, is enabled by moving the operating element.

In another embodiment of the invention, the operating element of the operating device has a microphone, so that the display of the medical image information can be influenced by voice control in addition to the influencing of the medical image information as a result of motions of the operating element.

In a further embodiment of the invention the operating device has an actuator with which the functional occupation of the aforementioned operating actuators of the operating element can be set (selected). The functional occupation of the operating actuators therefore is customized in an application specific fashion.

In an embodiments of the invention, electrical signals, which can be wirelessly transmitted via a transmission device at the operating element to a reception device of the operating device that is connected to a processor for processing the signals, are generated by operating an operating actuator and/or by speaking into a microphone. A facilitated handling of the operating element thus results, since a cable extending between the movable operating element and the signal processor, which is stationary relative to the operating element, is not present. Such a cable can cause stumbling or tripping.

In another embodiment of the invention the means for quantitatively determining the adjustment motion of the operating element determine the coordinates of the operating element in a reference coordinate system and transform these into coordinates of an image coordinate system that can be written into the medical image information. The means for quantitatively determining the adjustment motion can subject the coordinates that are determined with regard to the reference coordinate system and/or the coordinates that are determined with regard to the image coordinate system to a mean value filtering. Undesired, unsteady motions of the operating element by the operating person can be advantageously smoothed by the mean value filtering, so that sudden changes with respect to the display of the medical image information items at the display surface do not occur as a result of small unsteady motions.

In a further embodiment of the invention the means for the quantitative determination of the adjustment motion of the operating element can be adjusted such that the scope or limits of the adjustment motion, which is necessary in order to influence the display of a medical image information, can be prescribed. Therefore, the sensitivity of the operating device, namely the range of an adjustment motion of the operating element, regarding which the operating device responds for initiating an action, can also be adjusted in an application-specific fashion.

In further embodiments of the invention, the operating element is fashioned as a handheld operating element and is capsuled in a liquid-tight manner, so that the operating element can be utilized in environments in which contact of the operating element with fluids, such as body fluids, may occur. Due to the liquid-tight encapsulation of the operating element, the operating element is washable and easy to clean. Furthermore, the liquid-tight encapsulation makes it possible to sterilize the operating element in a simple way, so that it can be used in antiseptic environments such as operating rooms.

DESCRIPTION OF THE PREFERRED EMBODIMENTS

Figure 1:
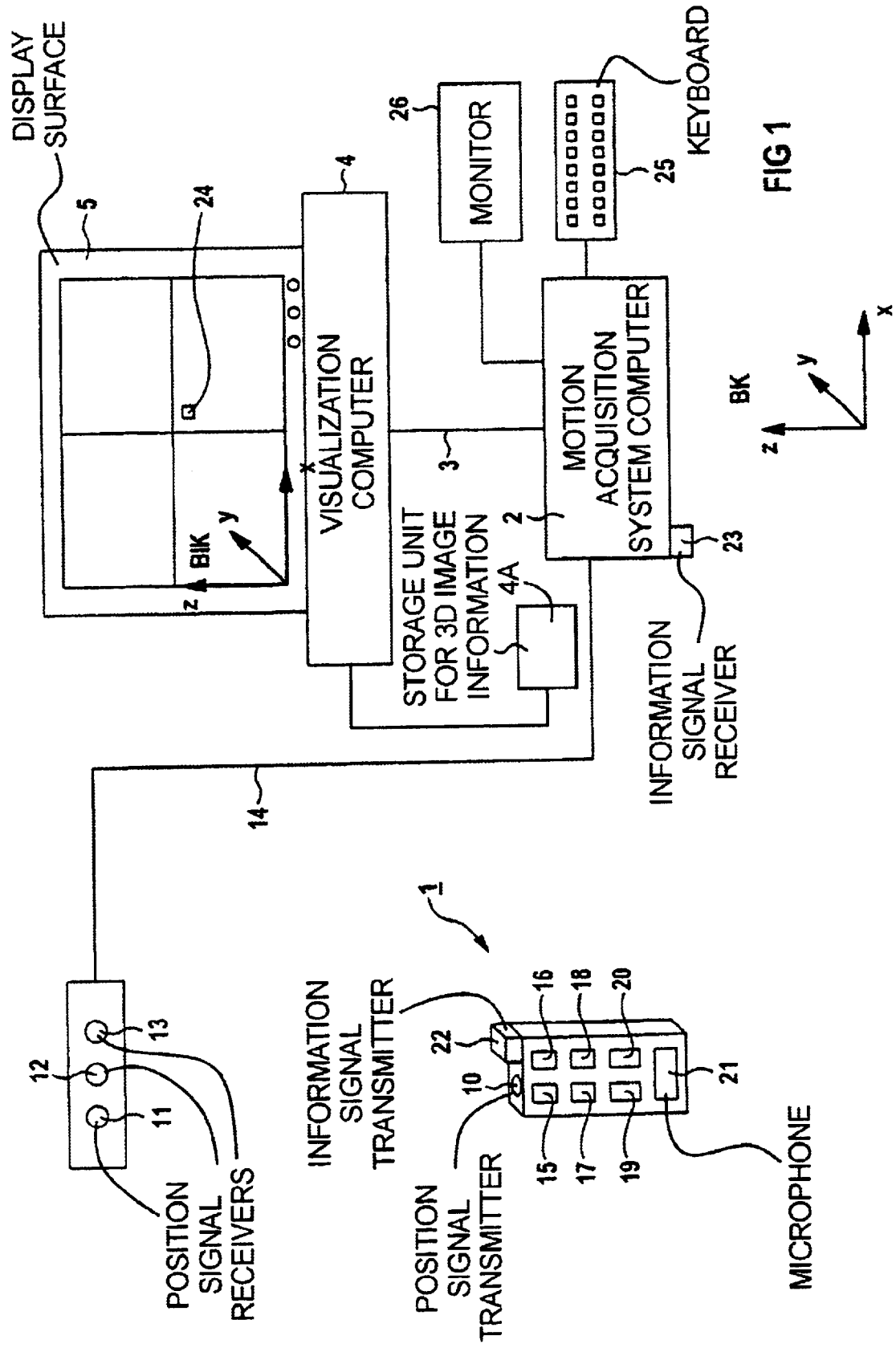
FIG. 1 is a schematic illustration of a medical workstation having an inventive operating device.

In the exemplary embodiment, the inventive operating device shown in FIG. 1 has a motion determining unit for quantitatively determining adjustment motions of an operating element 1, including a system computer 2. The operating device is provided for influencing the display of medical image information items, so that the system computer 2 is connected via a communication line 3 to a visualization computer 4.

Image data sets of three-dimensional anatomic objects, which have been determined by means of diagnostic devices and which can be represented in various representation forms at a display surface such as a projection screen, or which can be represented at a display screen of a display device, are stored in a storage unit 4A of the visualization computer 4. In the exemplary embodiment, a monitor 5 is connected to the visualization computer 4 for displaying the image information items.

Figure 2:
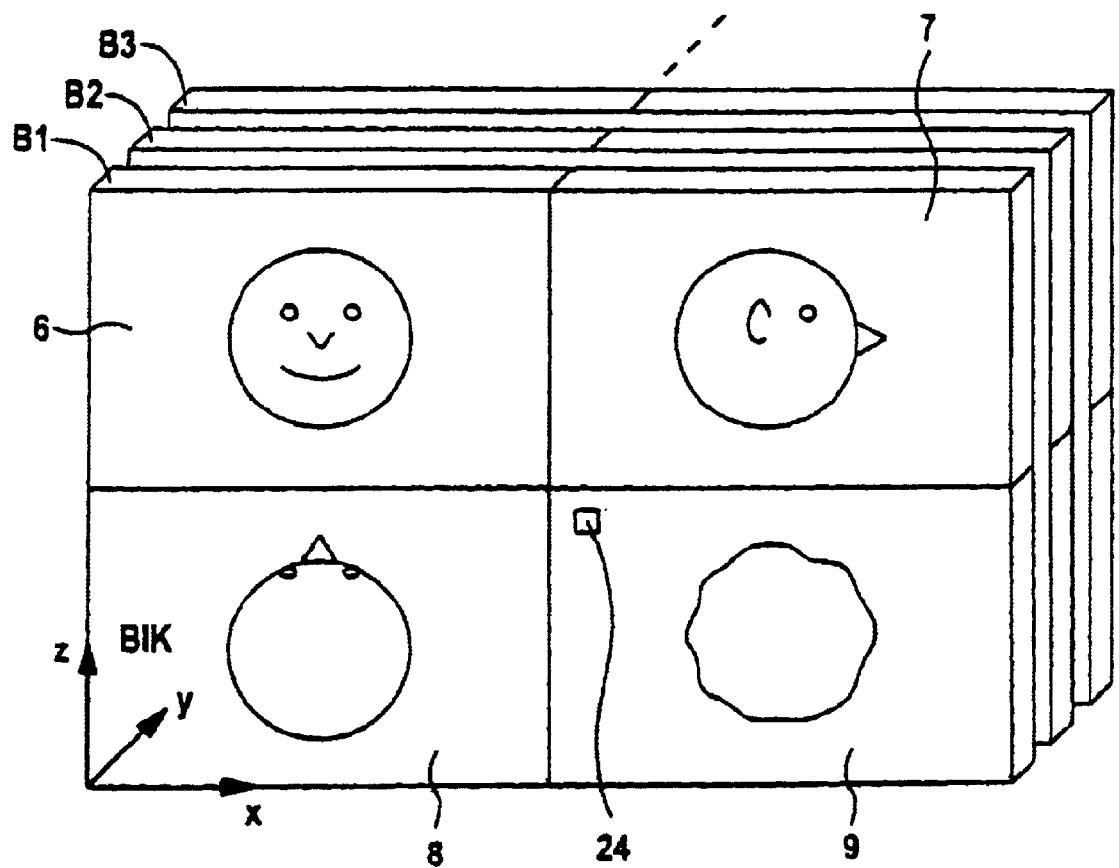
FIG. 2 shows an image set of three orthogonal 2D views and a 3D view of an object for explaining the invention.

For the exemplary embodiment, FIG. 2 shows an image data set B1, which is determined from a 3D image data set of the head of a patient (not shown), which comprises four sub-images and which is displayed at the monitor 5. The sub-images 6 to 8 are tomograms of the head of the patient that are visualized in three orthogonal views. The sub-image 6 shows a 2D view of a coronal image slice. The sub-image 7 shows a 2D view of a sagittal image slice. The sub-image 8 shows a 2D view of a transverse image slice. The sub-image 9 is a 3D view of a tissue area from the head of the patient. In FIG. 2, B2 and B3 indicate further image sets that are present in the visualization computer 4, which image sets show further views of the patient head corresponding to the image set B1 and which can be displayed at the screen of the monitor 5.

The inventive operating device is fashioned such that the medical image information items displayed at the screen of the monitor 5 can be influenced solely by motions of the operating element 1. In the exemplary embodiment, the operating element 1 is fashioned as a handheld operating element, which can be moved in six degrees of freedom. The operating element is encapsulated in a liquid-tight manner, since the operating element 1 is preferably provided for the utilization in operation rooms, in which it may come into contact with body fluids. Therefore, the operating element 1 is washable and easy to clean. As a result of the liquid-tight encapsulation, the operating element 1 can also be sterilized in a simple way, this being a condition for the utilization in an antiseptic environment.

In the exemplary embodiment, the motions of the operating element 1 are determined in a reference coordinate system for influencing the representation of the image information items displayed at the screen of the monitor 5. The coordinates of the operating element 1 can be determined by means of optical, electromagnetic position determination systems, which are known and are based on the reception and evaluation of infrared light or ultrasound. In the exemplary embodiment, the coordinates of the operating element 1 are determined in the reference coordinate system BK with the aid of a transmission device 10 of the operating element 1 that emits ultrasound signals and three ultrasound receivers 11 to 13, which are arranged at stationary locations relative to the operating element 1. The ultrasound receivers 11 to 13, whose positions in the reference coordinate system BK are known to the system computer 2, are connected via a line 14 to the system computer 2, so that the system computer 2 can determine the current position of the operating element 1, namely the current coordinates of the operating element 1, with respect to the reference coordinate system BK in realtime. This ensues by evaluating the ultrasound signals, which are received by the ultrasound receivers 11 to 13 and which are transmitted to the system computer 2, for example by transit time or phase measurements. Subsequently, the system computer 2 transforms the coordinates of the operating element 1, that are practically continuously determined during the operation of the operating device, with respect to the reference coordinate system BK into image coordinates of an image coordinate system BIK, which can be written into the displayed image information items. The system computer 2 subjects these coordinates, which have been determined relative to the image coordinate system BIK and which describe the motions of the operating element 1, to a mean value filtering in order to eliminate, by smoothing, any unsteady guidance of the operating element 1 by an operator. Such unsteadiness could have a disadvantageous effect, for example, by causing a sudden change (jump) of the image information items. Subsequently, the system computer 2 transmits the image coordinates, which characterize the motion of the operating element 1, to the visualization computer 2, which, corresponding to the determined image coordinates, changes the representation of the medical image information items on the monitor 5.

In order to selectively influence the image information items displayed at the monitor 5, the operating element 1 has six operating actuators in the form of keys 15 to 20, and a microphone 21. Electrical signals are generated in the operating element 1 by actuating one of the keys 15 to 20, or by speaking into the microphone 21. These signals are transmitted via a transmission device 22, that emits signal-carrying waves, to a reception device 23, that receives the signal-carrying waves. The reception device 23 is connected to the system computer 2, which evaluates the signals received from the reception device 23. Depending on the information items that are still to be explained and that are transmitted with the electrical signals to the system computer 2, the system computer 2 carries out corresponding adjustments, or transmits control commands influencing the representation of the image information items to the visualization computer 4.

If a user actuates the key 15 of the operating element 1, information items are transmitted via the transmission device 22 and the reception device 23 to the system computer 2 of the operating device, which information items place the operating device into a first operating mode, referred to as selection mode. In this mode, a marker in the form of a cursor 24 is faded into the medical image information items represented on the monitor 5. The marker 24 can be moved relative to the image information items when the operating element 1 is moved, and one of the sub-images 6 to 9, for example, can be selected, or other menu points of an operating mask that can be displayed at the monitor 5 can be selected and adjustments can be modified when the key 15 is operated again. For example, when the marker 24 is moved onto the sub-image 6 by moving the operating element 1 and when the key 15 is pushed again, the sub-image 6 is selected for the further processing.

If the key 16 is actuated, a zoom mode of the operating device is activated by appropriate information items transmitted from the operating element 1 to the system computer 2. In this mode, whereby the view of the sub-image 6 can be enlarged or reduced, for example by forward and backward motions of the operating element 1 in the y-direction of the reference coordinate system BK.

Given the actuation of the key 17 of the operating element 1, an object rotation mode is activated, in which a corresponding rotation of the sub-image 6 can be effected by rotations of the operating element 1, for example around the y-axis of the reference coordinate system BK. When the sub-image 9 is selected in the selection mode and when the object rotation mode is subsequently activated by operating the key 17, a corresponding rotation of the object, which is three-dimensionally visualized in the sub-image 9, is effected by arbitrary rotations of the operating element in space.

A fourth operating mode, referred to as slice positioning mode, of the operating device can be selected by actuating the key 18. This mode allows a scrolling through different views of image information items solely by moving the operating element 1. Depending on motions of the operating element 1 in the reference coordinate system BK, it is therefore possible to scroll through different tomograms that are generated from the 3D image data set and that are allocated to different image sets B1 to B3, as is indicated in FIG. 2 with the three image sets B1 to B3, which are generated from a 3D image data set and which comprise different tomograms of successively situated body slices of the patient. 2D views of sagittal image slices are scrolled when the operating element 1 is horizontally moved in the x-direction of the reference coordinate system BK; 2D views of transverse image slices are scrolled when the operating element 1 is vertically moved in the z-direction of the reference coordinate system and coronal image slices are scrolled when the operating element 1 is moved forward or backward in the y-direction of the reference coordinate system. Given diagonal motions of the operating element 1, the transverse, coronal and sagittal 2D views of image slices are simultaneously updated on the monitor 5 and therefore are run through.

Therefore, different operating modes of the operating device can be selected dependent on the actuation of one of the keys 15 to 18, and in each mode the medical image information items displayed at the monitor 5 can be influenced solely by motions of the operating element 1 in the slice positioning mode, the zoom mode and the object rotation mode in particular.

In the exemplary embodiment, a zeroing of the operating element 1 automatically ensues when one of the keys 15 to 18 is actuated, i.e., the system computer 2 determines all motions, which follow after one of the keys 15 to 18 has been operated, relative to the location of the operating element 1 at the time the corresponding key 15 to 18 was actuated. Such a zeroing of the operating element 1 also can be achieved in every operating mode by actuating another key, namely key 19.

Additionally, the functional occupation of the keys 15 to 18 can be in an application-specific manner varied. In the exemplary embodiment, the key 20 of the operating element is initially operated for this purpose. The keys 15 to 18 are to be subsequently actuated once after each other in a selected sequence. The selection mode is allocated to the key first actuated, the zoom mode is allocated to the second key actuated, the object rotation mode is allocated to the third key actuated and to the slice positioning mode is allocated to the fourth key actuated.

The microphone 21 is provided at the operating element 1 in order to increase the operating comfort, so that simple functions for influencing the representation of the medical image information items can also ensue in a voice-controlled manner. The voice signals transmitted to the system computer 2 via the transmission device 22 and reception device 23 are evaluated in a known manner and are transformed into control signals for the system computer 2 and the visualization computer 4.

The sensitivity of the operating device also can be adjusted with respect to the motion of the operating element 1 and the influence, which is associated therewith, on the representation of the medical image information items displayed at the monitor 5, so that a convenient guidance of the operating element 1 is possible. In the exemplary embodiment, a user can execute an adjustment program with keyboard 25 that is connected to the system computer 2 and with a monitor 26 that is connected to the system computer 2 so that for each operating mode of the operating device, the scope of an adjustment motion can be prescribed that is necessary to effect a corresponding change in the image representation. For example, the operating device can be adjusted such that a motion of the operating element 1 through 10 cm in one of the spatial directions of the reference coordinate system BK, in the selection mode, causes the marker 24 to move 5 cm in the corresponding direction of the image coordinate system BIK, which is written into the image information items, so that the ratio of the scope of the motion of the operating element 1 in the reference coordinate system BK to the scope of the motion of the marker 24 in the image coordinate system BIK is 2:1.

In the slice positioning mode, the adjustment can ensue, for example, such that a motion of the operating element 1 of 5 cm in one of the three spatial directions of the reference coordinate system BK is necessary for scrolling in different views of tomograms, i.e., for changing from one view of a tomogram into another view of a tomogram.

The sensitivity can be adjusted in a similar way for the zoom mode and for the object rotation mode. It is expedient for the object rotation mode to select the ratio of the motion of the operating element 1 in the reference coordinate system BK to the corresponding motion of the object in the image coordinate system BK as 1:1 so that the user does not lose orientation during rotations of the object, which is three-dimensionally displayed at the monitor 5.

In the exemplary embodiment, the adjustment motion of the operating element 1 is quantitatively determined with the aid of ultrasound signals. The adjustment motion alternatively can be quantitatively determined by optical position acquisition systems, electromagnetic position acquisition systems or by position acquisition systems that are based on infrared light. Furthermore, the adjustment motion of the operating element 1 can be quantitatively determined with inertial navigation systems such as acceleration sensors or gyroscopes.

Furthermore, the operating element 1 need not necessarily have operating actuators and a microphone. For example, if the operating element 1 has only a microphone, a changeover into the individual operating modes of the operating device can ensue in a voice-controlled fashion.

Moreover, further operating modes can be provided for the operating device.

The separation between the system computer 2 and the visualization computer is not necessary either. The visualization computer 4 alternatively can assume all functions of the system computer 2 if it has suitable computing capacity, so that only one computer is present.

Although other modifications and changes may be suggested by those skilled in the art, it is the intention of the inventors to embody within the patent warranted hereon all changes and modifications as reasonably and properly come within the scope of their contribution to the art.

We claim as our invention:

1. An operating device for use with a source of three-dimensional image information representing a medical image of a three-dimensional subject, for influencing display of said three-dimensional image displayed at a display surface, comprising:

a freely movable operating element, physically independent of said source, movable through arbitrary adjustment motions;

an adjustment motion acquisition system for quantitatively identifying said adjustment motions of said operating element; and a display surface on which said three-dimensional image information is displayed with a three-dimensional visual appearance at said display surface, said display surface being physically separate from said operating element and being connected to said adjustment motion acquisition system, and said three-dimensional visual appearance of said image information displayed on said display surface being alterable solely by said adjustment motions of said operating element identified by said adjustment motion acquisition system.

2. An operating device as claimed in claim 1 wherein said operating element is movable in six degrees of freedom.

3. An operating device as claimed in claim 1 wherein said adjustment motion acquisition system operates said display surface in a plurality of different modes, and wherein said freely movable operating element comprises a plurality of operating actuators which, when individually activated, respectively select one of said modes.

4. An operating device as claimed in claim 3 wherein said image information is displayable at said display surface in different use, and wherein one of said operating actuators, upon actuation thereof, causes said adjustment motor acquisition system to operate in a mode for scrolling through said different views.

5. An operating device as claimed in claim 3 wherein, upon actuation of one of said operating actuators, said motion acquisition system operates said display surface in a selection mode to allow an information item on said display surface to be selected solely by said adjustment motions of said operating element.

6. An operating device as claimed in claim 3 wherein, upon actuation of one of said operating actuators, said motion acquisition system operates said display surface in a zoom mode which allows a size of said image information on said display to be increased or decreased.

7. An operating device as claimed in claim 3 wherein, upon actuation of one of said operating actuators, said motion acquisition system operates said display surface in a rotation mode, allowing rotation on said display surface of at least one of said image information on said display solely by said adjustment motions of said operating element.

8. An operating device as claimed in claim 3 wherein, upon actuation of one of said operating actuators, said motion acquisition system operates said display surface to allow at least some of said image information on said display to be shown in different views on said display surface solely by said adjustment motions of said operating element.

9. An operating device as claimed in claim 3 wherein said operating element comprises a functional occupation actuator which, when actuated, allows selection of allocation of the respective operating actuators to said modes.

10. An operating device as claimed in claim 3 wherein said operating element comprises a wireless transmitter for emitting signals identifying respective actuation of said operating actuators and further comprising a receiver for receiving said signals and a signal processor connected to said receiver for evaluating said signals.

11. An operating device as claimed in claim 3 wherein said operating element further comprises a microphone for receiving spoken voice commands for influencing said image information on said display surface.

12. An operating device as claimed in claim 11 wherein said operating element comprises a transmitter for emitting wireless signals identifying respective actuation of said operating actuators and said voice commands, and further comprising a receiver for receiving said signals and a signal processor for evaluating said signal.

13. An operating device as claimed in claim 1 wherein said motion acquisition system comprises means for determining coordinates of said operating element in a reference coordinate system and for transforming said coordinates into coordinates of an image coordination system which is written into said image information on said display surface.

14. An operating device as claimed in claim 13 wherein said motion acquisition system comprises means for mean value filtering at least one of said coordinates of said operating element in said reference coordinate system and said coordinates of said operating element in said image coordinate system.

15. An operating device as claimed in claim 13 further comprising means for adjusting said motion acquisition system for selecting a scope of the adjustment motion of said operating element which is necessary for effecting a predetermined alteration of said image information on said display surface.

16. An operating device as claimed in claim 1 wherein said operating element is a hand-held operating element.

17. An operating device as claimed in claim 1 wherein said operating elements is encapsulated liquid-tight.

* * * * *